United States Patent
Chapoy et al.

(10) Patent No.: US 8,394,140 B2
(45) Date of Patent: Mar. 12, 2013

(54) PRE-FORMED INTRASTROMAL CORNEAL INSERT FOR CORNEAL ABNORMALITIES OR DYSTROPHIES

(75) Inventors: L. Lawrence Chapoy, Barrington Hills, IL (US); William M. Flynn, Downers Grove, IL (US)

(73) Assignee: Addition Technology, Inc., Des Plaines, IL (US)

( * ) Notice: Subject to any disclaimer, the term of this patent is extended or adjusted under 35 U.S.C. 154(b) by 1301 days.

(21) Appl. No.: 11/378,404

(22) Filed: Mar. 17, 2006

(65) Prior Publication Data
US 2007/0219631 A1  Sep. 20, 2007

(51) Int. Cl.
*A61F 2/14* (2006.01)
(52) U.S. Cl. .................................. 623/5.12; 623/5.11
(58) Field of Classification Search ............... 623/4.1, 623/5.11, 5.12, 5.13
See application file for complete search history.

(56) References Cited

U.S. PATENT DOCUMENTS

| | | | |
|---|---|---|---|
| 4,452,235 A | 6/1984 | Reynolds | |
| 4,671,276 A | 6/1987 | Reynolds | |
| 4,961,744 A | 10/1990 | Kilmer et al. | |
| 5,188,125 A | 2/1993 | Kilmer et al. | |
| 5,300,118 A | 4/1994 | Silvestrini et al. | |
| 5,312,424 A | 5/1994 | Kilmer et al. | |
| 5,318,047 A | 6/1994 | Davenport et al. | |
| 5,323,788 A | 6/1994 | Silvestrini et al. | |
| 5,403,335 A | 4/1995 | Loomis et al. | |
| 5,405,384 A | 4/1995 | Silvestrini | |
| 5,466,260 A | 11/1995 | Silvestrini et al. | |
| 5,475,452 A | 12/1995 | Kuhn et al. | |
| 5,505,722 A | 4/1996 | Kilmer et al. | |
| 5,592,246 A | 1/1997 | Kuhn et al. | |
| 5,599,341 A | 2/1997 | Mathis et al. | |
| 5,628,794 A | 5/1997 | Lindstrom | |
| 5,645,582 A | 7/1997 | Silvestrini et al. | |
| 5,653,752 A | 8/1997 | Silvestrini et al. | |
| 5,693,092 A | 12/1997 | Silvestrini et al. | |
| 5,766,171 A | 6/1998 | Silvestrini | |
| 5,785,651 A | 7/1998 | Kuhn et al. | |
| 5,824,086 A | 10/1998 | Silvestrini | |
| 5,846,256 A | 12/1998 | Mathis et al. | |
| 5,888,243 A | 3/1999 | Silverstrini | |
| 6,050,999 A | 4/2000 | Paraschac et al. | |
| 6,051,023 A | 4/2000 | Kilmer et al. | |
| 6,175,754 B1 | 1/2001 | Scholl et al. | |
| 6,206,919 B1 * | 3/2001 | Lee | 623/5.12 |
| 6,214,044 B1 | 4/2001 | Silverstrini | |

(Continued)

FOREIGN PATENT DOCUMENTS

WO  WO 93/12735  7/1993
WO  WO 2005/107648 A2  11/2005

*Primary Examiner* — David Isabella
*Assistant Examiner* — Joshua Levine
(74) *Attorney, Agent, or Firm* — Foley & Lardner LLP (57) ABSTRACT

A pre-formed intrastromal corneal insert for use in treating Keratoconus and similar dystrophies and methods of using the same. An intrastromal insert of the present invention comprises a biocompatible polymer and may be used to adjust corneal curvature, thereby correcting vision abnormalities caused by disease or other surgical procedures. The insert may be comprised of a circular or semi-circular ring shape or a portion of a ring, or "arc", encircling the anterior cornea within the frontal circumference of the cornea. The insert may be used in multiples to form complete arcs or to form constructs of varying thicknesses. The insert of the present invention possesses a cross section that results in a low scattering level of light.

33 Claims, 5 Drawing Sheets

U.S. PATENT DOCUMENTS

| | | |
|---|---|---|
| 6,231,582 B1 | 5/2001 | Gandiancoa et al. |
| 6,251,118 B1 | 6/2001 | Proudfoot et al. |
| 6,361,560 B1 * | 3/2002 | Nigam .................. 623/5.14 |
| 6,508,837 B1 * | 1/2003 | Silvestrini .................. 623/5.11 |
| 6,543,453 B1 * | 4/2003 | Klima et al. .................. 128/898 |
| 6,607,556 B1 * | 8/2003 | Nigam .................. 623/5.11 |
| 6,626,941 B2 * | 9/2003 | Nigam .................. 623/5.16 |
| 2002/0065555 A1 * | 5/2002 | Nigam .................. 623/5.11 |
| 2002/0107566 A1 * | 8/2002 | Nigam .................. 623/5.12 |
| 2002/0111677 A1 * | 8/2002 | Nigam .................. 623/5.12 |
| 2002/0116056 A1 | 8/2002 | Kirk |
| 2004/0034412 A1 * | 2/2004 | Schachar .................. 623/4.1 |
| 2004/0034413 A1 | 2/2004 | Christensen |
| 2004/0073303 A1 * | 4/2004 | Schanzlin et al. .................. 623/5.16 |
| 2004/0243231 A1 | 12/2004 | Koziol |

* cited by examiner

THICKNESS
FIG. 4b

PRE-FORMED INTRASTROMAL CORNEAL INSERT FOR CORNEAL ABNORMALITIES OR DYSTROPHIES

FIELD OF THE INVENTION

The present invention relates generally to inserts for use in correcting various corneal-related defects. More particularly, the present invention relates to intrastromal corneal inserts for use in treating Keratoconus and other corneal-related dystrophies.

BACKGROUND OF THE INVENTION

The cornea is the outermost fibrous transparent coating of the eye which resembles a watch glass. The curvature of the cornea is normally somewhat greater than the rest of the globe of the eye and is ideally spherical in nature. The central third of the cornea is referred to as the optical zone or visual pathway with a slight flattening taking place outwardly thereof as the cornea thickens towards its periphery. Most of the refraction of the eye takes place through the cornea.

Figure 1:
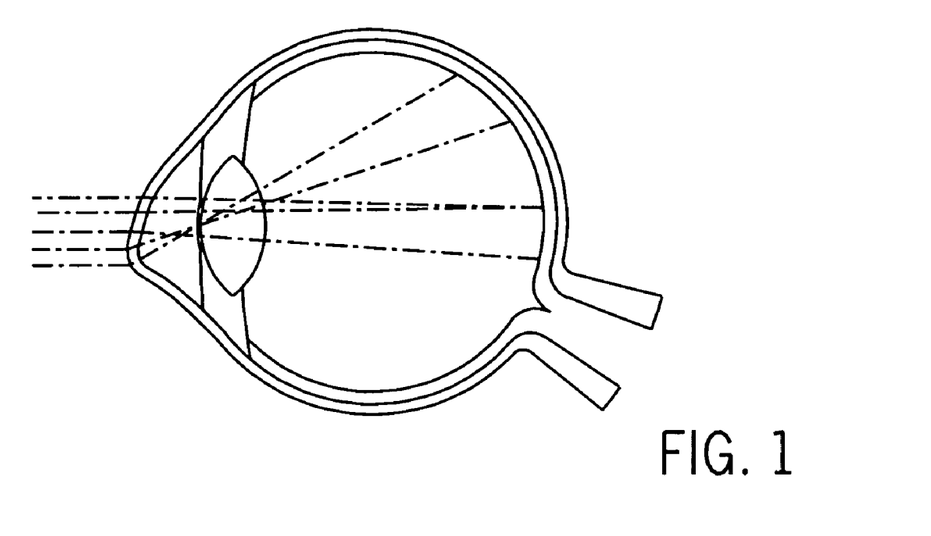
FIG. 1 is a representation showing how light rays pass through a Keratoconus, thin cornea eye, and are distorted due to the cone-like shape of the cornea.
Figure 2:
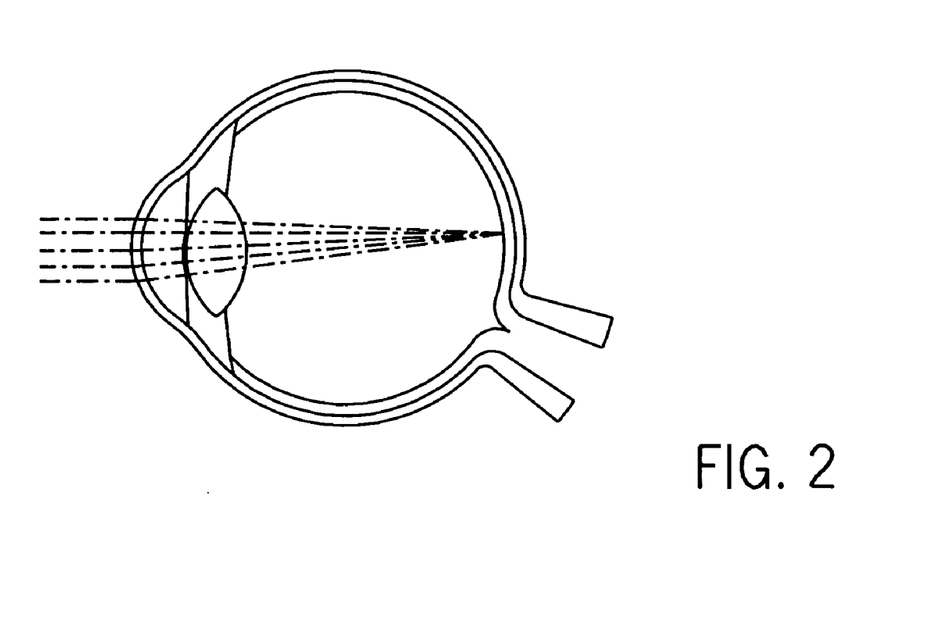
FIG. 2 is a representation showing how light rays pass through a normal, healthy eye, providing clear and focused vision.

There are a number of dystrophies which involve a gross deformation of the cornea and which cause severe vision problems. If allowed to progress, such dystrophies can lead to blindness. One of these dystrophies is Keratoconus, in which a bulge or cone develops on the cornea. For a cornea with Keratoconus, the corneal tissue is thin, and one's normal eye pressure pushing on the weakened thin tissue causes the bulge or cone. This results in complex reflections and scattering patterns of light entering the eye, which prevent the appropriate focusing of an image onto the retina, and the structure of the cornea is significantly weakened. This phenomenon is shown in FIG. 1. In contrast, FIG. 2 shows how light rays pass through the cornea in a healthy, normal eye, providing clear and focused vision. Severe forms of Keratoconus require the implantation of intrastromal or intracorneal ring segments or, in some instances, a corneal transplant. Less severe cases of Keratoconus have been largely addressed with custom-made hard contact lenses.

The cone in a Keratoconic eye manifests differently in each patient. In other words, the cone can vary by position both centrally, as opposed to radially, in addition to the angle as would be observed in a polar coordinate axis. The cone can also vary by size in the sense of the height of the protrusion, known as sagital depth, the cone's slope measured by a "K" or Keratometry reading, and the surface area of the footprint of the cone. In addition, the thickness of the cornea, although different for each individual, typically falls within a normal range. However, for a keratoconic cornea, the cornea is abnormally thin and contributes to its irregular shape in a patient-specific way. The thinning of the cornea affects the cornea's structural integrity, leads to the creation of a bulge or cone and the extenuating visual problems that result.

There are a number of other conditions which are similar to Keratoconus in nature. These conditions include ectasia (corneal thinning), post-LASIK ectasia, pellucid marginal degeneration and other corneal dystrophies. All of these dystrophies lead to gross deformities of the cornea with consequences similar to Keratoconus. Therefore, while the present application discusses Keratoconus in particular, it should be understood that the principles, products and procedures discussed herein are also applicable to other similar conditions.

One method for correcting these disorders is through the implantation of polymeric rings (intrastromal corneal rings) in the eye's corneal stroma to flatten, strengthen and change the curvature of the cornea. Previous work has involved the implantation of polymethylmethacrylate (PMMA) rings, allograft corneal tissue, and hydrogels for common refractive procedures: myopia, hyperopia and astigmatism. One of the ring devices that has been conventionally used involves a split ring design which is inserted into a channel that has been previously dissected in the stromal layer of the cornea. Such a ring is discussed in U.S. Pat. No. 5,824,086, in the name of Silvestrini. Other ring devices use PMMA intrastromal rings which completely encircle the cornea. Such ring designs are disclosed in U.S. Pat. Nos. 4,452,235 and 4,671,276, both in the name of Reynolds, and U.S. Pat. No. 4,961,744, in the name of Kilmer. In each of these rings, a minimally invasive incision is used both for producing a channel and for inserting the implant as a permanent refractive procedure for myopia, hyperopia and astigmatism. However, these rings are not designed for correction of various visual aberrations caused by Keratoconus or other conditions of the cornea, and these designs are not directed to the introduction of therapeutic or diagnostic materials into the corneal intrastromal space.

For corneas with gross deformities or abnormalities caused by corneal disease, there has been a need for an improved product and method for treating these abnormal keratoconic corneas, improve a patient's vision and avoid a treatment of last resort, i.e., a corneal transplant. In these more extreme cases, conventional intracorneal ring segments can normalize the shape of the cornea from within, add structural integrity, flatten the protruding cone and, in the process, eliminate many of the visual distortions and aberrations caused by Keratoconus and other corneal dystrophies, while also stabilizing the progression of Keratoconus.

Although conventional intracorneal ring segments can provide the benefits discussed above, they suffer from a number of technological deficiencies. For example, conventional intracorneal ring segments do not cause a sufficient amount of flattening or reshaping of the cornea when placed outside of the visual pathway or optical zone where light enters the eye. Although it has been determined that a more central placement of the intracorneal ring segments leads to greater flattening efficacy, all known ring segments generate halos, glare and unusual light scattering when placed near or inside the visual pathway, as light rays are defracted by the intracorneal rings themselves across the visual pathway of the eye. Each of these deficiencies make conventionally known and commercially available intracorneal ring segments inadequate in treating the visual problems caused by Keratoconus and other similar corneal dystrophies.

SUMMARY OF THE INVENTION

The present invention is directed to a pre-formed polymeric insert suitable for insertion between the lamella of the corneal stroma. The insert comprises a full or semi-circular ring or an arc-shaped segment of a ring and can be used in isolation, or in multiples, encircling a portion or all of the cornea. In the case of multiple inserts, the inserts can be of substantially uniform or of varying physical dimensions. The insert may comprise one or more synthetic or natural high-modulus biocompatible polymers. The ring inserts possess a low light scattering design and can be one of a contiguous shape or of varying physical dimensions across the arcuate.

These and other advantages and features of the invention, together with the surgical procedures, organization and manner of operation thereof, will become apparent from the following detailed description when taken in conjunction with the accompanying drawings, wherein like elements have like numerals throughout the several drawings described below.

DETAILED DESCRIPTION OF PREFERRED EMBODIMENTS

In order to make a smaller diameter intracorneal ring (in the range of less than 6.5 millimeters) work as an effective device, a compromise is required between the flattening and reshaping effect to the cornea when placed within the optical zone and a ring of a low light scattering design. Intracorneal ring segments constructed in accordance with this compromise address both the visual and physiological issues caused by Keratoconus. In particular, the present invention serves to provide minimal light diffraction while flattening a bulbous cornea into a more naturally reshaped cornea.

As used herein, certain terms may have the following defined meanings. As used in the specification and claims, the singular form "a," "an" and "the" include plural references unless the context clearly dictates otherwise. For example, the term "a segment" includes a plurality of segments, including mixtures thereof. It should also be noted that the term "ring portion" can refer to a segment of a ring or an entire ring.

As used herein, the terms "segment," "insert," and "ring," in the singular form or in plural are construed to have the same meaning. As used herein, the terms "intrastromal" and "intracorneal" will be construed to have the same meaning.

As used herein, the term "comprising" is intended to mean that the compositions and methods include the recited elements, but not excluding others. "Consisting essentially of" when used to define compositions and methods, shall mean excluding other elements of any essential significance to the combination. "Consisting of" shall mean excluding more than trace elements of other ingredients and substantial method steps for use of the devices of this invention. Embodiments defined by each of these transition terms are within the scope of this invention.

All numerical designations, e.g., arc, diameter, distance and the like are approximations which are varied (+) or (−) by increments of about five percent. It is to be understood, although not always explicitly stated, that all numerical designations are preceded by the term "about."

The corneal stroma is the third layer of the cornea, as well as the thickest layer. It is transparent and located within the middle of the cornea between Bowman's Membrane and Descemet' Membrane.

The corneal lamella is the uniform fibers made of collagen within the stroma. Pre-formed means that the ring and/or ring segments have been shaped or formed before being implanted into the cornea and whose dimensions are suitable in terms of shape, thickness, height, width and curvature for implantation into the cornea.

As used herein, circular means that the object is shaped substantially like a circle, with its radius being of equal length from all points along the outside surface of the object. As used herein, oval means a circular shape with its radius being of varying lengths from the outside surface of the object. As used herein, ellipsoidal means a cross-section of a ring which is circular in design, tapering off to two blunt end points adjacent to one another. As used herein, semi-ellipsoidal means a cross-section of a ring which is circular by design, tapering to one blunt end point on one side and remaining circular on the geometrically adjacent side. As used herein, arcuate means the arc of the ring from end to end and all points along the arc.

With respect to the high-modulus biocompatible polymers, the term high-modulus means a biocompatible polymer that is stiff with a moduli equal to or greater than about 3.5 kpsi. A biocompatible polymer is material that is physiologically suitable for introduction into the body. Examples of each include, but are not limited to, polymethylmethacrylate (PMMA), teflon, polycarbonate, polysulfones, epoxies, polyacrylates or polyefins such as polyethylene, polypropylene, polybutylene, and their mixtures and interpolymers. Many such materials have been used in the manufacturing of hard contact lenses. A hybrid device will be comprised of a low modulus material for the outer surface layer and a high modulus material for its inside core. For the outer layer of a hybrid device, the polymeric materials comprises low modulus polymers which have a modulus of elasticity less than about 3.5 kpsi, more preferably between about 1 psi and about 1 kpsi and most preferably between about 1 psi and about 500 psi, which are physically compatible with the eye. These biocompatible, low modulus materials include physiologically compatible elastomers and such cross-linked polymeric gels such as polyhydroxyethylmethylacrylate (Poly-HEMA) or polyvinylpyrrolidone (PVP), polyethylene oxide, or polyacrylates, polyacrylic acid and its derivatives, and their co-polymers, as well as biologic polymers such as cross-linked dextran, cross-linked heparin, or hyaluronic acid. Thermoplastic hydrogels include hydropolyacrylonitrile, polyvinyl alcohol derivatives, hydrophilic polyurethanes, stryrene-PVP block copolymers and the like.

Dimensions or physical dimensions shall mean the shape, thickness, height and width of a cross section of a ring segment.

Angled edge shall mean a blunt, rounded but angled end point on the outside surface of a ring along its arc. A spacing element shall mean a pre-formed object which is inserted between the corneal lamella causing it to spread.

One aspect of the present invention comprises a pre-formed polymeric insert suitable for insertion between the lamella of the corneal stroma, as well as a method for using such an insert. The insert comprises a full or semi-circular ring or an arc-shaped segment of a ring and can be used in isolation, or in multiples, encircling a portion or all of the cornea. In a further aspect, the one or more segments comprising the ring are of the same or different shape, thickness, height or width. Thus, in one aspect, the segment is of a length that when inserted into the eye is less than a complete 360° ring. In one aspect, the segment is of a length less than 360°, yet greater than 180°. In a further aspect, the segment is more than 1° yet less than 180°. Preferred segment size ranges include from about 270° to 355°, about 200° to 269°, about 140° to 199°, about 70° to 139°, and about 20° to 69°. In the case of multiple inserts and/or ring segments, the segments can be of the same or different size as defined by arcuate. They can also be of varying cross-sectional dimensions, meaning shapes, thicknesses, heights or widths, along the arcuate of the ring. The insert may comprise one or more segments that are individually or collectively comprised of high-modulus biocompatible polymers. In another aspect, the one or more inserts are "hybrid" because they comprise different layered materials, or alternatively or in addition, is hollow. Accordingly, the one or more segments can be one of a contiguous shape, thickness, height and width, or of varying dimensions across the arcuate.

By "low light scattering," the present invention is referring to designs that reduce clinical effects such as halos, glare, star-bursts, photophobia and poor night vision to the point that they do not materially degrade vision. It is known that smooth, edgeless, clear materials, such as PMMA, tend to provide even and predictable refraction of light. It is also known that edges, points or sharp angles create uneven, unpredictable stratification of light, also referred to as light diffraction or light scattering. As ring portions or segments are moved into the eye's optical zone to remediate the disease state of keratoconus, the one or more ring or ring segment's contour and shape must be designed to eliminate visual side affects and aberrations caused by light scattering due to their design and placement. Clinically, patients using prior art devices have identified halos, glare, star-bursts, photophobia and poor night vision, due to one's pupils widening in dark surroundings bringing the rings into view, as typical symptoms from known intrastromal rings. The term "low scattering" designs reduce the above mentioned clinical effects to the point that they do not materially degrade vision.

Figure 3A:
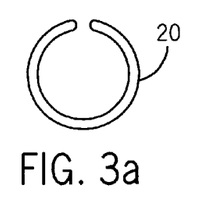
FIG. 3(a) is a top view of a circular ring segment of one thickness according to a first embodiment of the present invention.
Figure 3B:
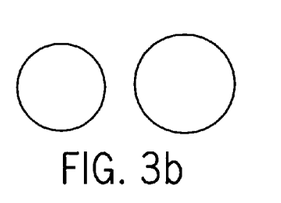
FIG. 3(b) is a cross-sectional view of the circular ring segment shown in FIG. 3(c), showing a cross-section at two different locations along a varying thickness ring segment according to an embodiment of the present invention.
Figure 3C:
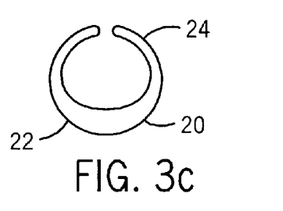
FIG. 3(c) is a top view of a circular ring of a varying thickness across its arcuate according to an embodiment of the present invention.
Figure 3D:
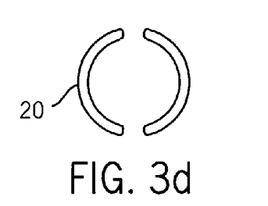
FIG. 3(d) is a top view of a pair of circular ring segments of a similar thickness according to an embodiment of the present invention.
Figure 3E:
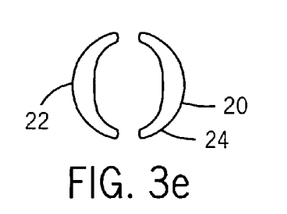
FIG. 3(e) is a top view of a pair of circular ring segments of a varying thickness across its arcuate according to an embodiment of the present invention.

In one embodiment of the present invention, and as shown in FIG. 3(a), a single ring segment 20 comprises a substantially circular cross section. In the embodiment shown in FIG. 3(a), the cross-section is substantially uniform throughout. In contrast, the ring segment 20 shown in FIG. 3(c) has a non-uniform cross-section, with the cross-section being larger at the base of the ring segment 22 than at the ends thereof 24. FIG. 3(b) shows the varying cross-section of the ring segment 20 of FIG. 3(c). The ring segments 20 shown in FIGS. 3(a) and 3(c) form substantially the entire ring for use in implantation. In FIGS. 3(d) and 3(e), two separate ring segments 20 are used to form the complete ring. In FIG. 3(d), the ring segments 20 have substantially circular and uniform cross-sections, while the ring segments 20 in FIG. 3(e) possess substantially circular but nonuniform cross sections.

Figure 4A:
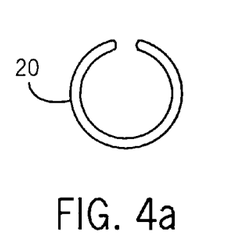
FIG. 4(a) is a top view of an oval-shaped ring segment of one thickness or of a varying thickness, across its arcuate according to another embodiment of the present invention.
Figure 4B:
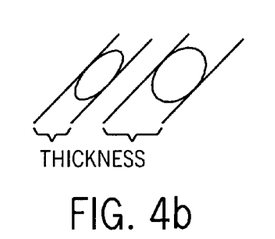
FIG. 4(b) is a cross-sectional view of oval shaped ring segments showing two cross sections, representing cross sections at two different locations along the arcuate of a varying thickness ring segment or the cross section of two separate and distinct ring segments of uniform thickness according to an embodiment of the present invention.
Figure 4C:
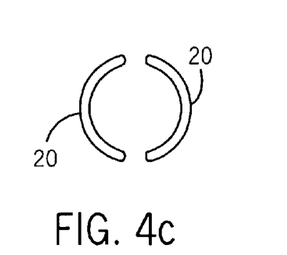
FIG. 4(c) is a top view of a pair of oval shaped ring segments of a similar thickness, or of a varying thickness, across its arcuate according to an embodiment of the present invention.

In another embodiment of the present invention, and as shown in FIG. 4(a), a single ring segment 20 has a substantially oval-shaped cross section. In the embodiment shown in FIG. 4(a), the cross section is substantially uniform throughout or of a varying thickness across its arcuate. The ring segment 20 shown in FIG. 4(a) forms substantially the entire ring for use in implantation. FIG. 4(b) shows cross-sections of ring segments 20 of FIGS. 4(a) and 4(c). Each of the cross sections in FIG. 4(b), when viewed separately, represent an oval-shaped, uniform cross section at any point along the ring. FIG. 4(b), when viewed together, represents a cross section at two different locations along the arcuate of a varying thickness ring segment. In FIG. 4(c), the ring segments 20 have oval-shaped and uniform cross sections or possess substantially oval-shaped but nonuniform cross sections. In FIG. 4(c), two separate ring segments 20 are used to form the complete ring.

Figure 5A:
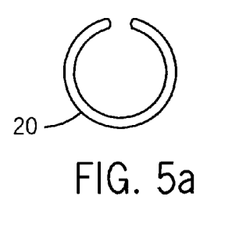
FIG. 5(a) is a top view of an ellipsoidal ring segment of one thickness or of a varying thickness, across its arcuate according to a third embodiment of the present invention.
Figure 5B:
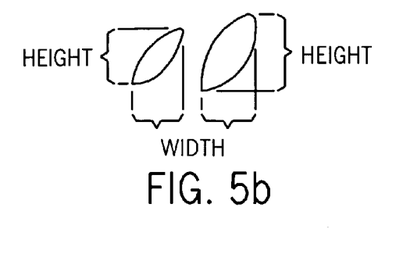
FIG. 5(b) is a cross-sectional view of the ring segments shown in FIG. 5(c), showing a cross section at two different locations along a ring segment with a varying thickness and height, or the cross section of two separate and distinct ring segments of uniform thickness and height according to an embodiment of the present invention.
Figures 5C, 5D, 5E:
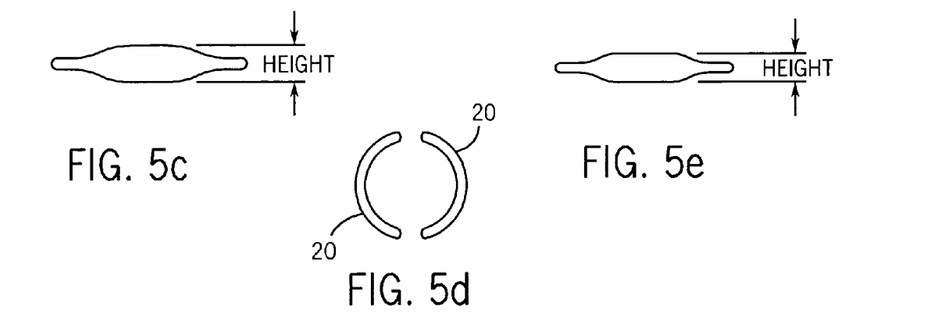
FIG. 5(c) is a side view of an ellipsoidal ring of a varying height across its arcuate according to an embodiment of the present invention.
FIG. 5(d) is a top view of a pair of ellipsoidal ring segments of a similar thickness, or of a varying thickness, across its arcuate according to an embodiment of the present invention.
FIG. 5(e) is a side view of an ellipsoidal ring segment, as shown in FIG. 5(d), of a varying height across its arcuate according to an embodiment of the present invention.

In another set of embodiments depicted in FIGS. 5(a)-5(e), each ring segment 20 has an ellipsoidal cross-section with angled ends (as opposed to the oval-shaped cross-sections shown in FIGS. 4(a)-4(c)), which minimizes or eliminates the light scattering and the affects of halos and glare due to its rounded angled edges. In the embodiment shown in FIG. 5(a), the cross-section is uniform throughout or of a varying thickness across its arcuate, or of a varying height across its arcuate, or of a varying thickness and height across its arcuate. The ring segments 20 shown in FIG. 5(a) form substantially the entire ring for use in implantation. FIG. 5(b) shows the cross-section of the ring segment 20 of FIG. 5(a) with a uniform width, and varying thickness and height. FIG. 5(c) represents a side view of the ring segment 20 of FIG. 5(a), with varying height. In FIG. 5(c), the width and thickness can be uniform or nonuniform. In FIG. 5(d), two separate ring segments 20 are used to form the complete ring. In the embodiment shown in FIG. 5(d), the ring segments 20 have substantially ellipsoidal cross sections with uniform widths, while ring thickness and height may be uniform or nonuniform. The side view of the ring segments 20 in FIG. 5(d) as shown in FIG. 5(e), possess a ellipsoidal cross section with a varying height. The thickness and width of the ring segment 20 in FIG. 5(e) are uniform or nonuniform.

Figure 6A:
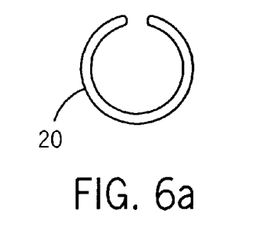
FIG. 6(a) is a top view of a semi-ellipsoidal ring segment of one thickness or height, or of a varying thickness and height, across its arcuate according to an embodiment of the present invention.
Figure 6B:
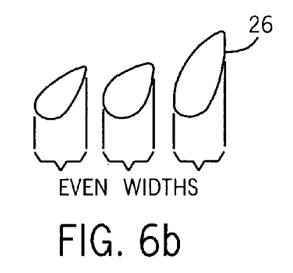
FIG. 6(b) is a cross-sectional view of semi-ellipsoidal ring segments showing three cross sections, representing cross sections at three different locations along the arcuate of a ring with different thicknesses and heights, or the cross section of three separate and distinct ring segments of uniform thicknesses and heights according to an embodiment of the present invention.
Figure 6C:
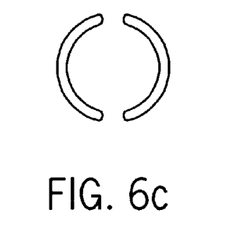
FIG. 6(c) is a top view of a pair of a semi-ellipsoidal ring segments of a similar thickness or height, or of a varying thickness and height, across its arcuate according to an embodiment of the present invention.
Figure 6D:
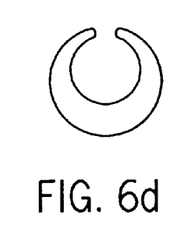
FIG. 6(d) is a top view of a semi-ellipsoidal ring segment with a varying cross sectional width across its arcuate according to an embodiment of the present invention, where the height and thickness can be uniform or nonuniform.
Figure 6E:
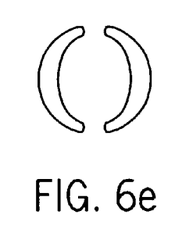
FIG. 6(e) is a top view of a pair of semi-ellipsoidal ring segments with a varying cross sectional width across their arcuate. For each segment, the thickness and height can be uniform or nonuniform according to an embodiment of the present invention.

In yet another embodiment of the present invention, and as shown in FIG. 6(a), a single ring segment 20 has a substantially semi-ellipsoidal cross section. In the embodiment shown in FIG. 6(a), the cross-sectional width is substantially uniform throughout. In FIG. 6(a), the cross sectional thickness and height may be uniform or nonuniform. The ring segments 20 shown in FIG. 6(a) forms substantially the entire ring for use in implantation. FIG. 6(b) shows three semi-ellipsoidal cross sections in which the thickness is different in all three drawings and the height and width are different. In FIG. 6(c), the two ring segments 20 which comprise the ring have substantially semi-ellipsoidal and uniform cross-sectional width. The height and thickness may be uniform or nonuniform. FIG. 6(d) shows a complete ring were the height and thickness may be uniform or nonuniform, but the width is nonuniform along the arcuate of the ring. FIG. 6(e) shows a pair of ring segments 20 where the height and thickness may be uniform or nonuniform, but the width is nonuniform along the arcuate of the ring.

A further embodiment of the present invention involves a ring design that varies in the cross-section of the ring segment 20 along the arcuate of the ring, which serves to flatten the cornea and to thicken the cornea specific to where it is thin. In other words, such a design provides a spacing element to compensate for unevenness in corneal tissue caused by disease and allows it to reshape the cornea to its natural shape. The physical dimensions of a full, semi-circular ring or arc shaped segment of a ring, meaning its cross sectional shape, thickness, height or width, may vary in any way to address deficiencies in corneal shape. One, more or all of these physical dimensions may vary along the arcuate of the ring. FIGS. 3(b), 4(b), 5(b) and 6(b) show various shapes and dimensions which may be altered for any ring design of this particular embodiment.

Yet another embodiment of the invention involves a ring design that is configured to match the refractive index of the intrastromal ring to that of the cornea. In this embodiment, the matching of the refractive index of the intrastromal ring to that of the cornea serves to eliminate halos, glare and light scattering, while still providing the same flattening effect necessary for the keratoconic cornea.

In addition to the above embodiments, it is also possible to incorporate an angled edge on the outer surface of the ring segments 20, with the back or adjacent end having more of a rounded architecture.

Figure 7:
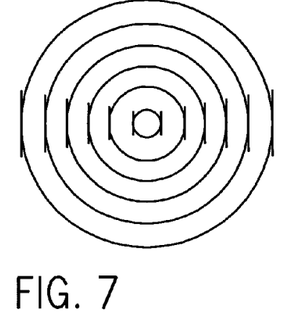
FIG. 7 is an elevational view of the optical zone at the center of a cornea, showing the placement locations of the ring or rings according to one embodiment of the present invention.

A variety of methods can be used to insert the ring segments of the present invention. For the purpose of illustration only, an intrastromal corneal insert of the present invention can be placed within the cornea of the eye as follows. First, a determination is made as to what shape the cornea should have in order for that eye to operate in an optically correct manner. This can be accomplished using any suitable method known in the art. For the purpose of illustration only, optical measurements of the eye can be taken, for example by using a topographical grid or topography of the type shown in FIG. 7, as well as pachymetry measurements for corneal thickness and optical refraction.

Figure 8:
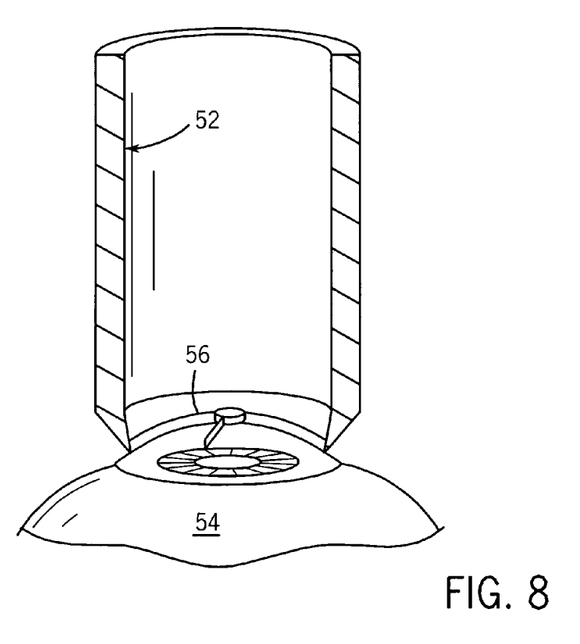
FIG. 8 is a representation of a cross section of an incision and placement marker that can be used to mark the initial incision placement on the cornea according to one embodiment of the present invention.
Figure 11:
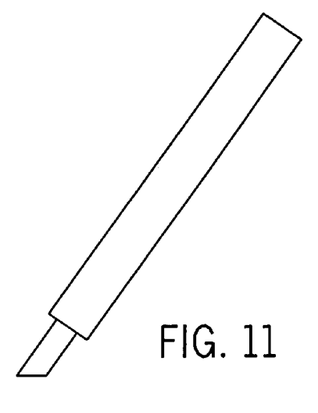
FIG. 11 is a representation of a diamond tipped scalpel that can be used in the implementation of the present invention.

The procedure, according to this embodiment of the invention begins with the geometric center of the cornea being marked using a placement and incision marker, as shown in FIG. 8. Next, working under a surgical microscope, a small (approximately 1 mm long and about 0.30 to 0.60 mm deep) incision is made using a diamond tip scalpel through the epithelium and Bowman's membrane of the cornea, as shown in FIG. 11. Such a scalpel is described in detail in U.S. Pat. No. 5,846,256, incorporated herein by reference in its entirety.

The incision is slightly larger than the ring segments 20 to be implanted and is made at a distance away from the geometric center equal to the radius of the ring from the same point. As an example, a 6.5 millimeter ring would be implanted through an incision at 3.25 millimeters from the geometric center, and a 5.5 millimeter ring would be implanted at 2.75 millimeters from the geometric center. Typically, the incision is made along the steep meridian as seen on a topographical map of the eye, temporally or superiorly depending upon the patient's condition.

Figure 9:
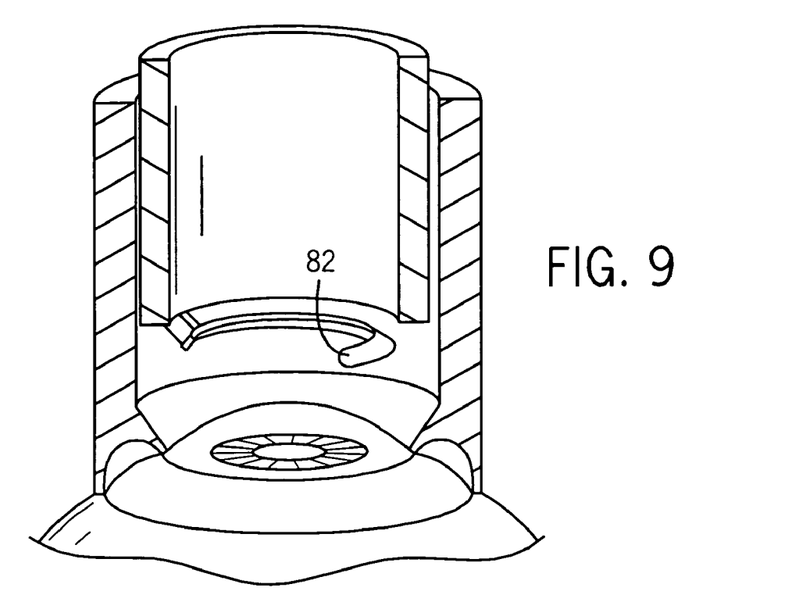
FIG. 9 is a cross sectional view of a centering guide and a corneal dissecting and rotating instrument used to create channels in the cornea in a clockwise direction.
Figure 10:
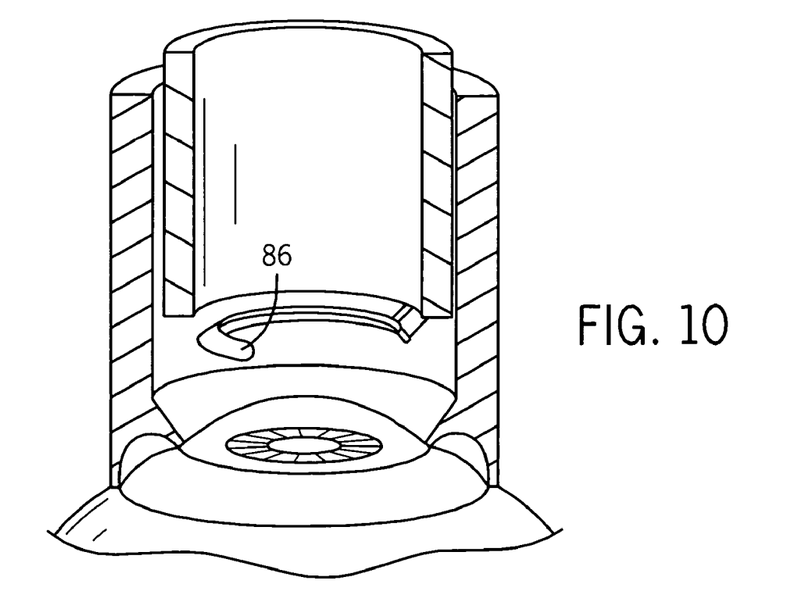
FIG. 10 is a cross sectional view of a centering guide and corneal dissecting and rotating instrument used to create channels in the cornea in a counterclockwise direction.

A channel is created within the corneal stroma by inserting a counter clockwise or clockwise corneal dissector blade 82 and gently threading it through and spreading the stroma lamella. The dissector blade 82 is threaded approximately two-thirds the way around the cornea circumferentially, as shown in FIG. 9. The dissector blade 82 is then removed by turning it in the reverse direction that it entered. A second dissector blade 86 is then threaded through the stroma lamella in the opposite direction again about two-thirds of the way circumferentially, as shown in FIG. 10. When placing arc segments greater than 180°, similar corneal dissectors are used which have a longer circumference. Another such dissector is shown in detail in U.S. Pat. No. 6,565,584 B1, FIGS. 17A, 17B, 18A and 18B.

With forceps, the intrastromal ring is threaded into the channel in one direction until completely seated in the channel. A second ring is then threaded into the opposite channel and both segments are placed in position by a standard Sinsky hook or similar instrument. Typically, intracorneal inserts contain small adjusting holes at their ends. Using a Sinsky hook, the surgeon can maneuver the inserts within the channels using these adjusting holes to get best placement. After placement of the segments, the single incision is then closed using a suture and is removed several weeks or months later depending on the healing process.

This procedure can be replicated with the use of a femtosecond laser. The laser will create tunnels in the cornea stroma through laser ablation beneath the surface of the cornea, thereby eliminating the incision marker and the need for manual dissection. The laser will also make the incision. The rings will be inserted and placed in position using forceps and the incision is closed using a suture.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments and with various modifications as are suited to the particular use contemplated.

What is claimed is:

1. An intrastromal implant shaped to be inserted within a human cornea and configured to alter the curvature of the cornea to effect refractive correction of an eye, comprising at least one pre-formed intracorneal ring portion formed from a polymeric material, the at least one pre-formed intracorneal ring portion having an arc shape with an inner diameter of less than about 6.5 millimeters and configured to encircle at least a portion of the cornea about the center of the cornea when implanted, the at least one pre-formed intracorneal ring portion characterized by a surface substantially free of sharp edges and points, and characterized by a cross-section that results in a low level of light scattering.

2. The intrastromal implant of claim 1, wherein the at least one intracorneal ring portion possesses a substantially uniform cross-section.

3. The intrastromal implant of claim 1, wherein the at least one pre-formed intracorneal ring portion possesses a nonuniform cross-section.

4. The intrastromal implant of claim 3, wherein the center of the at least one pre-formed intracorneal ring portion possesses a larger cross-section than the ends of the at least one pre-formed intracorneal ring portion.

5. The intrastromal implant of claim 1, wherein the at least one intracorneal ring portion possesses a substantially circular cross-section possessing angled ends.

6. The intrastromal implant of claim 1, wherein the at least one intracorneal ring portion possesses an oval-shaped cross-section possessing angled ends.

7. The intrastromal implant of claim 1, wherein the at least one pre-formed intracorneal ring portion possesses rounded ends and an ellipsoidal cross-section and wherein the at least one pre-formed intracorneal ring portion is free of points and edges.

8. The intrastromal implant of claim 1, wherein the at least one intracorneal ring portion possesses a semi-ellipsoidal cross-section possessing angled ends.

9. The intrastromal implant of claim 1, wherein the at least one pre-formed intracorneal ring portion comprises two ring portions configured to form an encircling ring to encircle at least a portion of the cornea, and wherein the encircling ring possesses an inner diameter of less than about 6.5 millimeters.

10. The intrastromal implant of claim 1, wherein the at least one pre-formed intracorneal ring portion comprises a synthetic high-modulus biocompatible polymer.

11. The intrastromal implant of claim 10, wherein the synthetic high-modulus biocompatible polymer is selected from the group consisting of polyacrylate, teflon, fluorinated ethylene propylene (FEP), polycarbonate, polysulfones, epoxies, polyolefins and mixtures and interpolymers thereof, with moduli greater than about 3.5 kpsi.

12. The intrastromal implant of claim 11, the at least one pre-formed intracorneal ring portion comprises polymethylmethacrylate (PMMA).

13. The intrastromal implant of claim 1, wherein the at least one pre-formed intracorneal ring portion comprises a high-modulus biocompatible polymer.

14. The intrastromal implant of claim 1, wherein the at least one pre-formed intracorneal ring portion is hollow.

15. The intrastromal implant of claim 1, wherein the at least one pre-formed intracorneal ring portion is shaped so that the refractive index of the at least one intracorneal ring portion matches the refractive index of the cornea.

16. The intrastromal implant of claim 1, wherein the at least one pre-formed intracorneal ring portion comprises a hybrid design, possessing a high modulus in a region of the ring portion that is closest to the center of the cornea when implanted and a lower modulus along the exterior of the ring portion farthest from the cornea when implanted.

17. The intrastromal implant of claim 1, wherein the at least one intracorneal comprises a single ring portion sized to form a ring around the cornea, and wherein the at least one intracorneal ring portion possesses a diameter of less than about 6.5 millimeters.

18. The intrastromal implant of claim 1, wherein the at least one intracorneal ring portion possesses a uniform thickness.

19. The intrastromal implant of claim 1, wherein the at least one intracorneal ring portion possesses a nonuniform thickness.

20. The intrastromal implant of claim 1, wherein the at least one intracorneal ring portion possesses a uniform height.

21. The intrastromal implant of claim 1, wherein the at least one intracorneal ring portion possesses a nonuniform height.

22. The intrastromal implant of claim 1, wherein the at least one intracorneal ring portion possesses a uniform width along its arcuate.

23. The intrastromal implant of claim 1, wherein the at least one intracorneal ring portion possesses a nonuniform width along its arcuate.

24. An intrastromal implant shaped to be inserted within a human cornea and configured to alter the curvature of the cornea to effect refractive correction of an eye, comprising at least one intracorneal ring portion formed from a polymeric material, possessing a predetermined shape characterized by a substantially smooth surface substantially free of sharp edges and points providing low light diffraction and a low level of light scattering, the at least one intracorneal ring portion having an arc shape defining a portion of an encircling ring, the encircling ring having a diameter of less than about 6.5 millimeters, the at least one intracorneal ring portion configured to encircle at least a portion of the cornea with at least a portion of the intracorneal ring portion disposed within the optical zone when implanted.

25. The intrastromal implant of claim 24, wherein the at least one intracorneal ring portion comprises a synthetic high-modulus biocompatible polymer.

26. The intrastromal implant of claim 24, wherein the at least one intracorneal ring portion is hollow.

27. The intrastromal implant of claim 24, wherein the at least one intracorneal ring portion comprises two ring portions sized to form the encircling ring around the cornea, and wherein the encircling ring possesses an inner diameter of less than about 6.5 millimeters.

28. The intrastromal implant of claim 24, wherein the at least one intracorneal ring portion comprises a hybrid design, possessing high modulus in a region of the ring portion that is closest to the center of the cornea when implanted and a lower modulus along the exterior of the ring portion farthest from the cornea when implanted.

29. The intrastromal implant of claim 24, wherein the at least one intracorneal ring portion possesses a nonuniform cross-sectional shape.

30. The intrastromal implant of claim 24, wherein the at least one intracorneal ring portion possesses a uniform cross-sectional shape.

31. The intrastromal implant of claim 1, wherein the at least one pre-formed intracorneal ring portion comprises a rounded end portion, a first portion and a second portion disposed along a length of the arc between the rounded end portion and the first portion, and wherein the first portion is characterized by a substantially uniform cross-section of a first size and the second portion is characterized by a substantially uniform cross-section of a second size.

32. The intrastromal implant of claim 24, wherein the at least one intracorneal ring portion possesses an ellipsoidal cross-section having rounded ends free of points and edges.

33. The intrastromal implant of claim 24, wherein the intracorneal ring portion comprises a rounded end region, a first region disposed about a portion of the arcuate and characterized by a substantially uniform cross-section of a first size, a second region disposed about another portion of the arcuate between the rounded end region and the first region and characterized by a substantially uniform cross-section of a second size, and a transition region disposed between the first and the second regions.

* * * * *

UNITED STATES PATENT AND TRADEMARK OFFICE
CERTIFICATE OF CORRECTION

| | | |
|---|---|---|
| PATENT NO. | : 8,394,140 B2 | Page 1 of 1 |
| APPLICATION NO. | : 11/378404 | |
| DATED | : March 12, 2013 | |
| INVENTOR(S) | : Chapoy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1375 days.

Signed and Sealed this

Thirteenth Day of January, 2015

Michelle K. Lee
*Deputy Director of the United States Patent and Trademark Office*